United States Patent
Bilgin et al.

(10) Patent No.: US 9,938,458 B2
(45) Date of Patent: Apr. 10, 2018

(54) CERAMIC SCINTILLATOR FIBER

(71) Applicant: Siemens Healthcare GmbH, Erlangen (DE)

(72) Inventors: Cansu Bilgin, Erlangen (DE); Juergen Leppert, Forchheim (DE); Christian Schroeter, Bamberg (DE); Stefan Wirth, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/492,248

(22) Filed: Apr. 20, 2017

(65) Prior Publication Data

US 2017/0313938 A1    Nov. 2, 2017

(30) Foreign Application Priority Data

Apr. 27, 2016  (DE) .................. 10 2016 207 173

(51) Int. Cl.
*G01T 1/20* (2006.01)
*C09K 11/77* (2006.01)
(Continued)

(52) U.S. Cl.
CPC ........ *C09K 11/7706* (2013.01); *A61B 6/4208* (2013.01); *C04B 35/44* (2013.01); *C04B 35/547* (2013.01); *C04B 35/6264* (2013.01); *C04B 35/62236* (2013.01); *C04B 35/62272* (2013.01); *C04B 35/638* (2013.01); *C04B 35/6342* (2013.01); *C04B 35/63448* (2013.01); *C04B 35/64* (2013.01); *C09J 163/00* (2013.01); *C09K 11/7701* (2013.01); *D01F 9/08* (2013.01); *G01T 1/20* (2013.01); *C04B 2235/3222* (2013.01); *C04B 2235/3224* (2013.01); *C04B 2235/3286* (2013.01); *C04B 2235/446* (2013.01); *C04B 2235/524* (2013.01);
(Continued)

(58) Field of Classification Search
CPC .............. A61B 6/4208; C09K 11/7701; C09K 11/7706; G01T 1/20
See application file for complete search history.

(56) References Cited

U.S. PATENT DOCUMENTS 5,496,502 A *  3/1996  Thomson .............. G01T 1/203
                                              250/361 R
7,573,035 B2 *  8/2009  Levene .................. G01T 1/201
                                              250/361 R
(Continued)

FOREIGN PATENT DOCUMENTS

DE         10021938 A1    12/2000
DE    102004020468 A1    11/2004
(Continued)

OTHER PUBLICATIONS

German Office Action for 10 2016 207 173 4 dated Jan. 20, 2017.
German Office Action. 10-2016-207-173.4. dated Jan. 20, 2017.

Primary Examiner — Marcus Taningco
(74) Attorney, Agent, or Firm — Harness, Dickey & Pierce, P.L.C.

(57) ABSTRACT

A method is for the production of a scintillator fiber. In an embodiment, the method includes provisioning a suspension of a binder dissolved in a solvent and a scintillator material; and pressing the suspension into a precipitation bath in which the binder is insoluble.

20 Claims, 4 Drawing Sheets

(51) Int. Cl.
  *A61B 6/00* (2006.01)
  *C04B 35/44* (2006.01)
  *C04B 35/547* (2006.01)
  *C04B 35/622* (2006.01)
  *C04B 35/626* (2006.01)
  *C04B 35/634* (2006.01)
  *C04B 35/638* (2006.01)
  *C04B 35/64* (2006.01)
  *C09J 163/00* (2006.01)
  *D01F 9/08* (2006.01)

(52) U.S. Cl.
  CPC .......................... *C04B 2235/5224* (2013.01); *C04B 2235/604* (2013.01); *C04B 2235/612* (2013.01); *C04B 2235/9646* (2013.01); *D10B 2101/08* (2013.01); *D10B 2509/00* (2013.01)

(56) References Cited

U.S. PATENT DOCUMENTS

| | | | |
|---|---|---|---|
| 9,611,168 B2* | 4/2017 | Morse | C03B 37/01262 |
| 2002/0102395 A1 | 8/2002 | Duclos | |
| 2003/0020044 A1* | 1/2003 | Lyons | C03C 10/00 252/301.5 |
| 2004/0218712 A1 | 11/2004 | Jiang et al. | |
| 2009/0014662 A1* | 1/2009 | Suhami | G01T 3/06 250/390.11 |
| 2013/0126753 A1* | 5/2013 | Aylward | B32B 37/1284 250/458.1 |
| 2016/0096148 A1 | 4/2016 | Schuetz et al. | |

FOREIGN PATENT DOCUMENTS

| | | |
|---|---|---|
| DE | 102013010735 A1 | 1/2015 |
| WO | WO-2009008911 A9 | 3/2009 |

* cited by examiner

CERAMIC SCINTILLATOR FIBER

PRIORITY STATEMENT

The present application hereby claims priority under 35 U.S.C. § 119 to German patent application number DE 102016207173.4 filed Apr. 27, 2016, the entire contents of which are hereby incorporated herein by reference.

FIELD

Embodiment of the invention generally relate to a method for the production of a scintillator fiber, a method for the production of a scintillator unit, a scintillator unit, an X-ray detector and a medical device.

BACKGROUND

Integrating indirect-conversion X-ray detectors can be used in X-ray imaging, for example in computed tomography, angiography or radiography. The information contained in the local modulation of the incident X-rays is detected by the X-ray detector, wherein the X-ray detector converts the information into a digital signal. In indirect-conversion X-ray detectors, the X-rays or the photons can be converted into light by a suitable converter material and into electric pulses by means of photodiodes. The converter material used is frequently scintillators, for example GOS ($Gd_2O_2S$), CsJ, YGO or LuTAG.

A scintillator unit comprises the converter material. Scintillators are in particular used in medical X-ray imaging in the energy range up to 1 MeV. Typically, so-called indirect-conversion X-ray detectors, so-called scintillator detectors, are used with which the conversion of the X-rays or gamma rays into electric signals takes place in two stages. In a first stage, the X-ray or gamma quanta are absorbed in a sub-region of the scintillator unit and converted into optically visible light, a quantity of light—this effect is known as luminescence. The light excited by luminescence is then converted in a second stage into an electric signal by a first photodiode or photomultiplier optically coupled to the scintillator unit in a sub-region of an evaluation unit, read-out via evaluation electronics or readout electronics and then forwarded to a computing unit.

Scintillators, for example cesium iodide deposited from the gas phase, can have anisotropic light conduction. Cesium iodide has a needle-shaped structure. As a result of this anisotropic light conduction, the quantity of light is not propagated laterally and hence the incident X-rays' positional information is retained. However, cesium iodide is not suitable for all modalities in medical imaging. For example, it is unsuitable for computed tomography since it neither has neither the necessary absorption properties nor a sufficiently stable signal response.

Suitable ceramic scintillators, such as, for example gadolinium gallium aluminum garnet (GGAG), comprise isotropic light conduction. It is also possible to use GOS as a ceramic scintillator. To retain the incident X-rays' positional information, the scintillator unit has a complicated structure. Generally, sawing processes are used to separate volume units, which define the pixels of the X-ray detector. The interstices can be filled with a reflecting material.

The sub-regions of the scintillator unit and the evaluation unit are as a rule subdivided such that a sub-region of the evaluation unit is assigned to each sub-region of the scintillator unit. This is then called a pixelated X-ray detector. X-ray detectors, such as those used in computed tomography, for example, are typically constructed from a plurality of modules comprising a stray radiation grid, a scintillator unit, an evaluation unit with photosensors or photodiodes, for example as a photodiode array, and with electronic units for converting the analog signals into digital information and a mechanical support. The stray radiation grid is used to suppress stray radiation. The mechanical support is used to assemble the stray radiation grid, the scintillator unit and the evaluation unit. The stray radiation grid, scintillator unit and photodiode are typically pixelated in the same way in two directions, for example into rectangular or quadratic pixels. In order to achieve good dose utilization with a simultaneously low degree of crosstalk between the pixels, the stray radiation grid, scintillator unit and photodiode are positioned very precisely with respect to one another when constructing the modules.

Known from WO 2009008911 A2 is a bundle of drawn fibers that have unagglomerated nanocrystallite scintillation particles in glass or plastic cores with a maximum spacing of 0.1 µm. The bundle of drawn fibers also comprises a cladding with X-ray absorbing mixtures in the cladding composition. Optionally, covering the bundle can prevent light from emerging at the X-ray incidence side while the X-rays are able to pass into the fiber core. To image the light exiting the fiber bundle at submicron intervals, it is preferable to use light expansion by way of a lens system or a fiber bundle expander. However, due to the numerous optical interfaces formed by the embedding of the scintillator particles in the plastic or glass matrix of the fiber core, a large portion of the light leaves the fibers due to the scatter. In addition, light conduction by longer fibers such as those required for the absorption of typical X-ray energy in computed tomography are no longer possible.

SUMMARY

Embodiments of the invention disclose a method for the production of a scintillator fiber, a method for the production of a scintillator unit, a scintillator unit, an X-ray detector and/or a medical device enabling improved light conduction and alternative structuring of the scintillator unit.

At least one embodiment of the invention is directed to a method for the production of a scintillator fiber; at least one embodiment of the invention is directed to a method for the production of a scintillator unit; at least one embodiment of the invention is directed to a scintillator unit; at least one embodiment of the invention is directed to an X-ray detector; and at least one embodiment of the invention is directed to a medical device.

At least one embodiment of the invention relates to a method for the production of a scintillator fiber comprising the steps of the provision of a suspension of a binder dissolved in a solvent and a scintillator material and of pressing the suspension into a precipitation bath, in which the binder is insoluble. During the pressing step, a scintillator fiber is formed as a green body. The pressing can in particular be compression molding or a shaping step. During the pressing step, the suspension is pressed into the precipitation bath. For example, the suspension can be pressed into precipitation bath by means of a screw or another pressure-generating mechanism.

At least one embodiment of the invention further relates to a method for the production of a scintillator unit comprising the steps of bundling a plurality of scintillator fibers according to at least one embodiment of the invention, in particular sintered scintillator fibers, and filling the interstices between the plurality of scintillator fibers with an adhesive. In the bundling step, a plurality of scintillator fibers according to at least one embodiment of the invention is first laid parallel in a mold. Vibration can be used to sort the scintillator fibers or distribute them uniformly in the mold so that a fiber bundle forms. It is then possible to exert pressure from the outside onto the fiber bundle in order to pack the bundle as tightly as possible. In the filling step, the interstices between the scintillator fibers are filled with an adhesive comprising, for example, an epoxy compound. A scintillator unit made up of a plurality of scintillator fibers is provided, wherein the arrangement of the scintillator fibers with respect to one another is fixed by the adhesive. The scintillator fibers can have different diameters. It is advantageously possible to achieve a high packing density of the fiber bundle in that the interstices between scintillator fibers with a larger diameter can be filled by scintillator fibers with a smaller diameter.

At least one embodiment of the invention further relates to a scintillator unit produced with the method according to at least one embodiment of the invention. The advantages of the method according to the invention or the advantages of the scintillator unit produced with the method according to at least one embodiment of the invention can be transferred to the scintillator unit according to the invention. It is advantageously possible to achieve inexpensive and simple structuring of the scintillator unit.

At least one embodiment of the invention further relates to an X-ray detector comprising a scintillator unit according to at least one embodiment of the invention and further comprising a evaluation unit. Each sub-region or pixel of the scintillator unit can include a plurality of scintillator fibers. A plurality of scintillator fibers can be assigned to one sub-region of the evaluation unit. It is advantageously possible for the quantity of light released in the scintillator fiber to be registered or evaluated in the one sub-region of the evaluation unit.

At least one embodiment of the invention further relates to a medical device comprising an X-ray detector according to at least one embodiment of the invention. The advantages of the X-ray detector according to the invention can advantageously be transferred to the medical device. It is advantageously possible to reduce the production costs of the medical device.

BRIEF DESCRIPTION OF THE DRAWINGS

The following explains example embodiments of the invention in more detail with reference to drawings, which show.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for the production of a scintillator fiber comprising the steps of the provision of a suspension of a binder dissolved in a solvent and a scintillator material and of pressing the suspension into a precipitation bath, in which the binder is insoluble. During the pressing step, a scintillator fiber is formed as a green body. The pressing can in particular be compression molding or a shaping step. During the pressing step, the suspension is pressed into the precipitation bath. For example, the suspension can be pressed into precipitation bath by means of a screw or another pressure-generating mechanism.

The inventors have recognized that the production of scintillator fibers can avoid complicated structuring of the scintillator unit. It is possible for a ceramic or a ceramic scintillator to be sintered, wherein the green body is present as a scintillator fiber. The green body can be tightly sintered after the debinding.

According to at least one embodiment of the invention, a solution of a binder and a solvent is produced. The binder can, for example, be a plastic that can be dissolved in the solvent. The solution is added to the scintillator material. The scintillator material can be present as a powdered luminescent material and/or as a powdered scintillator material. Agitation, the application of ultrasound or a central mixer can be used to mix the scintillator material homogeneously and bubble-free with the solution to form a suspension. The suspension can then be pressed into a precipitation bath through a nozzle with a defined cross section and a defined diameter. The solvent can diffuse out of the suspension into the precipitation bath. In the precipitation bath, preferably up to 90 percent of the solvent can be removed from the suspension. The binder can be precipitated as a solid and bind the scintillator material. The scintillator material can be surrounded by the binder. The scintillator material can be uniformly distributed in the binder.

Advantageously, the reflections of the scintillation light or the light quanta of the quantity of light can enable a preferred light conduction along the fiber direction on the walls of the scintillator fiber. Advantageously, it is possible to avoid complex structuring of the scintillator unit. The costs of the production of the detector or scintillator unit can advantageously be reduced. During the method steps and further method steps, a straight alignment of the scintillator fibers achieves a particularly advantageous quality of the scintillator fibers.

According to one embodiment of the invention, the method further comprises the step of the solidification of the scintillator fiber. The solidification step can include a drying step. In the solidification step, liquid components, such as solvent and precipitation bath, can be removed from the green body or the scintillator fiber. Any residual solvent in the green body can be removed from the green body in the solidification or drying step. Advantageously, components that are no longer required for further steps can be removed from the scintillator fiber. Advantageously, the scintillator fiber can be prepared for subsequent steps. Advantageously, it is possible to remove components from the scintillator fiber that are no longer required for further steps. Advantageously, the scintillator fiber can be prepared for subsequent steps. Advantageously, it is possible to reduce the content of materials that do not correspond to the scintillator material.

According to one embodiment of the invention, the method further comprises at least one of the steps: debinding the scintillator fiber, first pressing of the scintillator fiber and sintering the scintillator fiber.

In the debinding step, the binder is at least partially, preferably completely, removed from the scintillator fiber. In the debinding step, the binder can be thermally decomposed. For example, when polysulfone is used as the binder, the polysulfone can be oxidized into water, carbon dioxide and sulfur dioxide by thermal decomposition. Following the debinding step, the scintillator fiber is present as a porous green body.

In the first pressing step, the scintillator fiber can be compacted. The first pressing can be cold isostatic pressing. During cold isostatic pressing, pressure can be applied on all sides of the scintillator fiber for compaction, wherein the cold isostatic pressing is performed in flexible, closed molds at room temperature in a pressure vessel filled with water. It is in particular possible for pores in the scintillator fiber to be compacted by means of the first pressing. In the sintering step, it is advantageously possible for disruptive pores to be compacted or reduced. It is advantageously possible to achieve a scintillator fiber with a greater density and/or fewer pores.

The sintering can be pressure-less sintering wherein the ambient air pressure can prevail. The sintering is performed at temperatures below the melting point of the scintillator material. In the case of gadolinium gallium aluminum garnet (GGAG), the sintering can, for example, take place at 1600 to 1800° C. The scintillator material gadolinium gallium aluminum garnet (GGAG) can be doped with cerium. To achieve a theoretical or optimal density of the scintillator fiber, with pressure-less sintering, a density of at least 95% of the theoretical or possible density of the scintillator material should be achieved. The sintered scintillator fiber can be free of binder and solvent. The binder and the solvent can burn off completely in the sintering step. The sintered scintillator fiber can contain scintillator material only. The scintillator fiber is advantageously very suitable for the detection of X-rays and has particularly good absorption properties.

According to one embodiment of the invention, the method comprises the sintering step and further the step of the second pressing of the scintillator fibers. The second pressing can be a second sintering step or hot isostatic pressing. During the second pressing, secondary compaction of the scintillator fiber can take place, for example by hot isostatic pressing. With hot isostatic pressing, hot pressing and sintering can be performed simultaneously. In this case, the scintillator fiber is placed in a deformable tight vessel. This vessel comes in a heatable autoclave and the component can be compacted at a defined temperature and a defined pressure of 100 to 200 MPa under inert gas protection. In this way, the gas pressure acts on all sides of the scintillator fiber so that the component is endowed with isotropic properties. It is advantageously possible to achieve a particularly high density of the scintillator fiber. The scintillator fiber can advantageously have isotropic properties. The pressing step differs from potential first pressing and second pressing steps in that, in the pressing step, the green body or the scintillator fiber is produced, formed and/or molded. In the potential first pressing and second pressing steps, the scintillator fiber that has already been produced is compacted.

According to one embodiment of the method according to the invention, the solvent comprises at least one element from the group consisting of aprotic polar solvent and N-methylpyrrolidone. The solvent can comprise an aprotic polar solvent, for example the aprotic, strongly polar organic solvent N-methylpyrrolidone. The binder comprises at least one element from the group consisting of amorphous high-performance thermoplastic and polysulfone. The binder polysulfone is soluble in aprotic polar solvents, for example chloroform, dichloromethane, N-methyl-2-pyrrolidone and dimethylacetamide. The scintillator material comprises at least one element from the group consisting of ceramic scintillator material, GGAG and GOS. The solution of binder and solvent can comprise polysulfone and N-methylpyrrolidone, wherein between 1 and 30 percent, for example percent by weight or percent by volume, polysulfone can be dissolved in N-methylpyrrolidone. The precipitation bath comprises at least one element from the group consisting of protic solvent, water, ethanol and isopropanol. The precipitation bath can comprise water or water/ethanol mixtures. When polysulfone is used as the binder, the precipitation bath can comprise ethanol, isopropanol, water or mixtures thereof. The water-soluble N-methylpyrrolidone can diffuse out of the suspension into the precipitation bath, the plastic or the binder can be precipitated as a solid and the scintillator material can be bound. Advantageously, the scintillator material can be bound in the binder. Advantageously, pressing the suspension into the precipitation bath can result in the formation or molding of scintillator fibers.

According to one embodiment of the method according to the invention, the solvent comprises at least one element from the group consisting of protic solvent, ethanol and isopropanol. The binder comprises at least one element from the group consisting of polyvinyl acetals and polyvinyl butyral. Polyvinyl butyrals with a low degree of acetalization are water-soluble; highly acetalized resins dissolve in alcohols. The scintillator material comprises at least one element from the group consisting of ceramic scintillator material, GGAG and GOS. The precipitation bath comprises at least one element from the group consisting of protic solvent and water. The precipitation bath can comprise water. When polyvinyl butyral is the binder, the solvent can comprise ethanol or isopropanol. For a suspension of polyvinyl butyral, the precipitation bath can comprise water. Advantageously, the scintillator material can be bound in the binder. Advantageously, pressing the suspension into the precipitation bath can result in the formation or molding of scintillator fibers.

According to one embodiment of the method according to the invention, the second pressing is performed at a gas pressure of 1 to 2000 bar. The scintillator fiber can advantageously be compacted.

According to one embodiment of the method according to the invention, in the solidification step, the scintillator fiber is dried at a temperature of between 20° C. and 130° C. The solvent and the precipitation bath can advantageously be at least partially removed from the scintillator fiber or the surface thereof.

According to one embodiment of the method according to the invention, the debinding is performed in air at a temperature of between 500° C. and 1000° C. The binder can advantageously be at least partially removed from the scintillator fiber.

According to one embodiment of the method according to the invention, the sintering is performed at a temperature of 1600° C. to 1800° C. The binder and the solvent can advantageously burn off or be removed completely in the sintering step.

According to one embodiment of the method according to the invention, the diameter of the scintillator fiber is 40 to 100 μm. The diameter or the thickness of the scintillator fibers can be selected with respect to acceptable optical crosstalk with an adjacent scintillator fiber in a scintillator unit. In particular the diameter of the sintered scintillator fibers can be 40 to 100 μm. The nozzle diameter for pressing the suspension into the precipitation bath can correspondingly be greater than the diameter of the sintered scintillator fibers, for example the nozzle diameter can be 75 to 150 μm. The sintering of the scintillator fiber can result in a volume shrinkage of 40 to 55 percent compared to the diameter of the scintillator fibers which is effected by the nozzle in the step of pressing the scintillator fiber into the precipitation bath. It is advantageously possible to achieve a diameter of the sintered scintillator fibers that enables the structuring of the scintillator unit from scintillator fibers, wherein one or more scintillator fibers can be assigned to a sub-region of the evaluation unit or the scintillator unit. The length of the scintillator fibers can be selected arbitrarily since it is possible to produce an infinite scintillator fiber with the method according to an embodiment of the invention.

At least one embodiment of the invention further relates to a method for the production of a scintillator unit comprising the steps of bundling a plurality of scintillator fibers according to at least one embodiment of the invention, in particular sintered scintillator fibers, and filling the interstices between the plurality of scintillator fibers with an adhesive. In the bundling step, a plurality of scintillator fibers according to at least one embodiment of the invention is first laid parallel in a mold. Vibration can be used to sort the scintillator fibers or distribute them uniformly in the mold so that a fiber bundle forms. It is then possible to exert pressure from the outside onto the fiber bundle in order to pack the bundle as tightly as possible. In the filling step, the interstices between the scintillator fibers are filled with an adhesive comprising, for example, an epoxy compound. A scintillator unit made up of a plurality of scintillator fibers is provided, wherein the arrangement of the scintillator fibers with respect to one another is fixed by the adhesive. The scintillator fibers can have different diameters. It is advantageously possible to achieve a high packing density of the fiber bundle in that the interstices between scintillator fibers with a larger diameter can be filled by scintillator fibers with a smaller diameter.

According to one embodiment of the method according to the invention, the adhesive comprises an epoxy compound. The epoxy can advantageously be resistant to X-rays. The adhesive can comprise a reflector material. The reflector material can advantageously reduce or prevent crosstalk from light quanta of the quantity of light from one scintillator fiber to an adjacent scintillator fiber. The adhesive can contain a filler able to absorb X-rays to a similar degree or in a similar order of magnitude as the scintillator fibers. It is advantageously possible to reduce the incidence of X-rays on the evaluation unit.

According to one embodiment of the method according to the invention, the method further comprises at least one of the steps: sawing in order to set the layer thickness of the scintillator unit and application of a reflector layer. In the sawing step, the scintillator fibers or the bundle comprising a plurality of scintillator fibers can in particular be sawn perpendicular to the direction of the length of the scintillator fibers or with a predetermined sawing edge angle with respect to the direction of the length of the scintillator fibers. The layer thickness of the scintillator unit can be set in the sawing step.

It is preferably possible to set or form a layer thickness of from 20 μm to 1000 μm. It is advantageously possible for the layer thickness to be that required to absorb the incident X-rays as completely as possible. An optical reflector or a reflector layer can be formed on the surface facing the X-rays. It is advantageously possible to avoid or reduce the ingress of a quantity of light from the outside into the scintillator fiber. The scintillator unit can comprise two sawn surfaces so that the scintillator unit has two flat surfaces. The flat surfaces can face the radiation source or the evaluation unit. It is advantageously possible for the scintillator unit to be connected to the evaluation unit in a planar manner.

At least one embodiment of the invention further relates to a scintillator unit produced with the method according to at least one embodiment of the invention. The advantages of the method according to the invention or the advantages of the scintillator unit produced with the method according to at least one embodiment of the invention can be transferred to the scintillator unit according to the invention. It is advantageously possible to achieve inexpensive and simple structuring of the scintillator unit.

At least one embodiment of the invention further relates to an X-ray detector comprising a scintillator unit according to at least one embodiment of the invention and further comprising a evaluation unit. Each sub-region or pixel of the scintillator unit can include a plurality of scintillator fibers. A plurality of scintillator fibers can be assigned to one sub-region of the evaluation unit. It is advantageously possible for the quantity of light released in the scintillator fiber to be registered or evaluated in the one sub-region of the evaluation unit.

At least one embodiment of the invention further relates to a medical device comprising an X-ray detector according to at least one embodiment of the invention. The advantages of the X-ray detector according to the invention can advantageously be transferred to the medical device. It is advantageously possible to reduce the production costs of the medical device.

Figure 1:
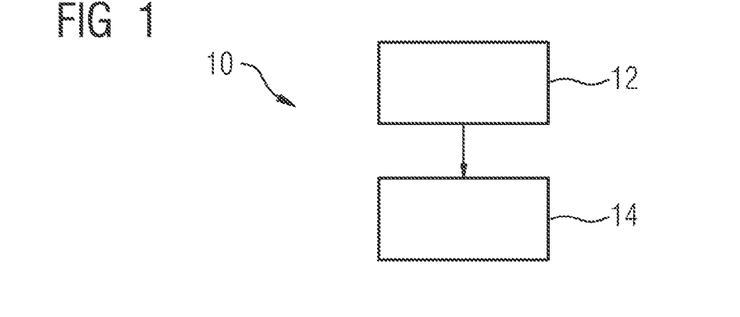
FIG. 1 a schematic view of a method according to the invention for the production of a scintillator fiber in a first embodiment.

FIG. 1 shows an example embodiment of the method according to the invention 10 for the production of a scintillator fiber in a first embodiment. The method 10 comprises the steps of the provision 12 of a suspension of a binder dissolved in a solvent and a scintillator material and pressing 14 the suspension into a precipitation bath in which the binder is insoluble. During this, a scintillator fiber is formed as a green body. The provisioning step 12 can comprise the production of the solution or the suspension.

A solution is produced from a binder and a solvent. The solution is added to the scintillator material. The scintillator material is present as powdered luminescent material or as powdered scintillator material. Agitation, the application of ultrasound or a centrifugal mixer is used to mix the scintillator material homogeneously and free from bubbles into the solution so that a suspension forms. The suspension provided is then pressed through a nozzle with a defined cross section and a defined diameter in the pressing step 14 into a precipitation bath. The solvent diffuses out of the suspension into the precipitation bath. In the precipitation bath, preferably up to 90 percent of the solvent can be removed from the suspension.

The binder or the plastic is precipitated as a solid and binds the scintillator material. The scintillator material is surrounded by plastic or binder. The scintillator material is uniformly distributed in the binder. In the pressing method step 14 and any possible further subsequent method steps, a straight alignment of the scintillator fibers achieves a particularly good quality of the scintillator fibers or the scintillator unit with scintillator fibers in straight alignment.

The solvent comprises at least one element from the group consisting of aprotic polar solvent and N-methylpyrrolidone. The solvent comprises an aprotic polar solvent, for example the aprotic, strongly polar organic solvent N-methylpyrrolidone. The binder comprises at least one element from the group consisting of amorphous high-performance thermoplastic and polysulfone. The binder polysulfone is soluble in aprotic polar solvents, for example chloroform, dichloromethane, N-methyl-2-pyrrolidone and dimethylacetamide. The scintillator material comprises at least one element from the group consisting of ceramic scintillator material, GGAG and GOS. The solution of binder and solvent preferably comprises polysulfone and N-methylpyrrolidone, wherein between 1 and 30 percent, for example percent by weight or percent by volume, polysulfone can be dissolved in N-methylpyrrolidone. The precipitation bath comprises at least one element from the group consisting of protic solvent, water, ethanol and isopropanol. The precipitation bath preferably comprises water or water/ethanol mixtures. When polysulfone is the binder, the precipitation bath preferably comprises ethanol, isopropanol, water or mixtures thereof. The water-soluble N-methylpyrrolidone diffuses out of the suspension into the precipitation bath, the plastic or the binder is precipitated as a solid and the scintillator material is bound.

The diameter of the scintillator fiber is 40 to 100 µm. The diameter or the thickness of the scintillator fibers can be selected in dependence on acceptable optical crosstalk with an adjacent scintillator fiber in a scintillator unit. In particular the diameter of the sintered scintillator fibers is 40 to 100 µm. The nozzle diameter for pressing the suspension into the precipitation bath can correspondingly be greater than the diameter of the sintered scintillator fibers, for example the nozzle diameter is 75 to 150 µm. The sintering 20 of the scintillator fiber can result in a volume shrinkage of 40 to 55 percent compared to the diameter of the scintillator fibers which is effected by the nozzle in the step of pressing 14 the scintillator fiber into the precipitation bath. The length of the scintillator fibers can be selected as desired.

In an alternative embodiment another solvent, another binder and another precipitation bath can be used. The solvent comprises at least one element from the group consisting of protic solvent, ethanol and isopropanol. The binder comprises at least one element from the group consisting of polyvinyl acetals and polyvinyl butyral. Polyvinyl butyrals with a low degree of acetalization are water-soluble; highly acetalized resins dissolve in alcohols. The scintillator material comprises at least one element from the group consisting of ceramic scintillator material, GGAG and GOS. The precipitation bath comprises at least one element from the group consisting of protic solvent and water. The precipitation bath preferably comprises water. When polyvinyl butyral is the binder the solvent preferably comprises ethanol or isopropanol. The precipitation bath for a suspension of polyvinyl butyral preferably comprises water.

Figure 2:
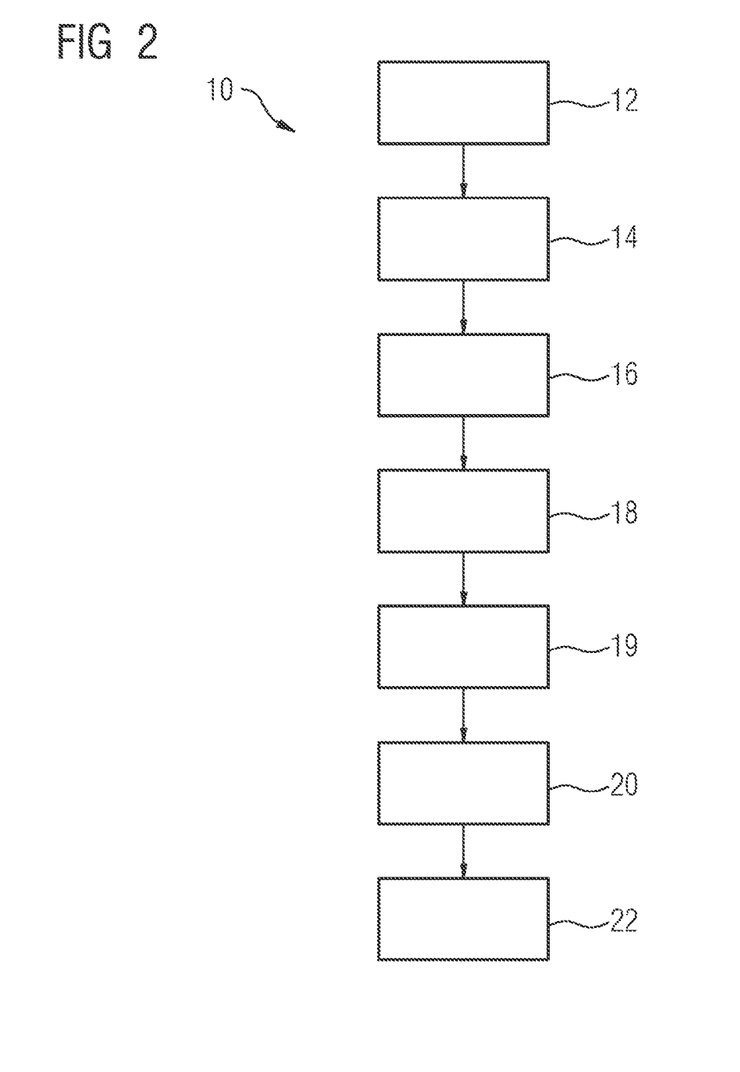
FIG. 2 a schematic view of a method according to the invention for the production of a scintillator fiber in a second embodiment.

FIG. 2 shows an example embodiment of the method according to the invention 10 for the production of a scintillator fiber in a second embodiment. The method 10 further comprises step of the solidification 16 of the scintillator fiber. The solidification step 16 preferably characterizes a drying step. In the solidification step 16, the scintillator fiber is dried at a temperature of between 20° C. and 130° C. In the solidification step 16, liquid components, such as solvent and precipitation bath, can be removed from the green body or the scintillator fiber. Any residual solvent in the green body can be removed from the green body in the solidification step 16 or drying step. The solidification step 16 takes place following the pressing 14. The method 10 further comprises the steps of the debinding 18 of the scintillator fiber, the first pressing 19 of the scintillator fiber, and the sintering 20 of the scintillator fiber.

The debinding step 18 takes place following the solidification step 16. In the debinding step 18, the binder is at least partially, preferably completely, removed from the scintillator fiber. The debinding 18 is performed in air at a temperature of between 500° C. and 1000° C. In the debinding step 18, the polysulfone is thermally decomposed and thereby oxidized into water, carbon dioxide and sulfur dioxide. Following the debinding step 18, the scintillator fiber is present as a porous green body.

The first pressing step 19 takes place following the debinding step 18. In the first pressing step 19, the scintillator fiber is compacted. The first pressing 19 can be cold isostatic pressing. During cold isostatic pressing, pressure can be applied to all sides of the scintillator fiber for compaction, wherein the cold isostatic pressing is performed in flexible, closed molds at room temperature in a pressure vessel filled with water. In particular, pores in the scintillator fiber are compacted by means of the first pressing.

The sintering step 20 takes place following the first pressing step 19. The sintering 20 can be pressure-less sintering, wherein the ambient air pressure can prevail. The sintering 20 takes place at temperatures below the melting point of the scintillator material. The sintering 20 is performed at a temperature of 1600° C. to 1800° C. In the case of gadolinium gallium aluminum garnet (GGAG), which can be doped with cerium, the sintering 20 can, for example, take place at 1600 to 1800° C. To achieve a theoretical or optimal density of the scintillator fiber, with pressure-less sintering, at least a density of 95% of the theoretical or possible density should be achieved. The sintered scintillator fiber is free of binder and solvent. The binder and the solvent burn off completely in the sintering step 20. The sintered scintillator fiber only contains scintillator material and possibly traces of binder, solvent or the precipitation bath.

The second pressing step 22 takes place following the sintering step 20. The second pressing 22 can be a second sintering step or hot isostatic pressing. During the second pressing 22, secondary compaction of the scintillator fiber, for example by means of hot isostatic pressing, can take place. With hot isostatic pressing, hot pressing and sintering can be performed simultaneously. In this case, the scintillator fiber is placed in a deformable tight vessel. This vessel comes in a heatable autoclave and the component can be compacted at a defined temperature and a defined pressure of 100 to 200 MPa under inert gas protection compacted. In this way, the gas pressure acts on all sides on the scintillator fiber so that the component is endowed with isotropic properties. The second pressing 22 is performed at a gas pressure of 1 to 2000 bar.

Figure 3:
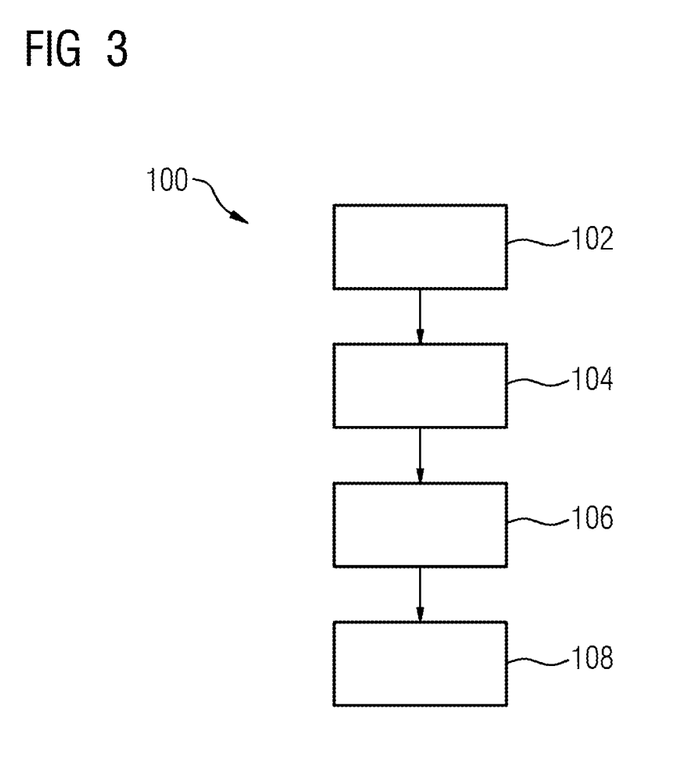
FIG. 3 a schematic view of a method according to an embodiment of the invention for the production of a scintillator unit.

FIG. 3 shows an example embodiment of the method according to the invention for the production of a scintillator unit. The method 100 for the production of a scintillator unit comprises the steps of the bundling 102 of a plurality of scintillator fibers according to an example embodiment of the invention, in particular sintered scintillator fibers, and the filling 104 the interstices between the plurality of scintillator fibers with an adhesive 2. In the bundling step 102, a plurality of scintillator fibers according to the invention is first laid parallel in a mold. Vibration can be used to sort the scintillator fibers or distribute them uniformly in the mold so that a fiber bundle is formed by the scintillator fibers. It is then possible to exert pressure from the outside onto the fiber bundle in order to pack the bundle as tightly as possible. In the filling step 104, the interstices between the scintillator fibers are filled with an adhesive. The adhesive is preferably an epoxy. The adhesive can comprise a reflector material. The adhesive can contain a filler able to absorb X-rays to a similar degree or in a similar order of magnitude as the scintillator fibers. A scintillator unit made up of a plurality of scintillator fibers is provided wherein the arrangement of the scintillator fibers with respect to one another is fixed by the adhesive.

The scintillator fibers can have different diameters.

The method 100 further comprises the steps of sawing 106 in order to set the layer thickness scintillator unit and of the application 108 of a reflector layer 4. The sawing step 106 takes place following the filling step 104. In the sawing step 106, the scintillator fibers or the bundle comprising a plurality of scintillator fibers can in particular be sawn perpendicular to the direction of the length of the scintillator fibers or with a predetermined sawing edge angle with respect to the direction of the length of the scintillator fibers. The layer thickness of the scintillator unit can be set in the sawing step 106. In this context, the layer thickness designates the thickness along which the X-rays are at least partially absorbed. The layer thickness is between 20 µm and 1000 µm. A optical reflector or a reflector layer is embodied on the surface of the scintillator unit facing the X-rays.

Figure 4:
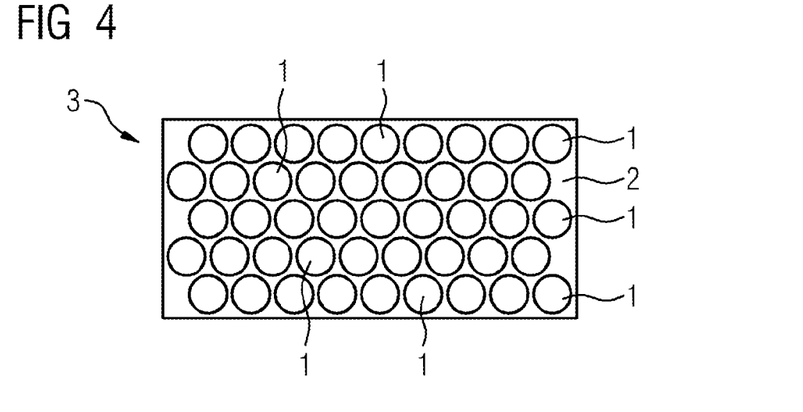
FIG. 4 a schematic top view of a scintillator unit according to an embodiment of the invention.

FIG. 4 shows a top view of an example embodiment scintillator unit 3 according to the invention. The scintillator fibers 1 are surrounded by an adhesive 2. The scintillator unit 3 comprises two sawn surfaces so that the scintillator unit 3 has two flat surfaces. The flat surfaces can face the radiation source of the medical device or the evaluation unit of the X-ray detector. The scintillator unit 3 is connected to the evaluation unit in a planar manner.

Figure 5:
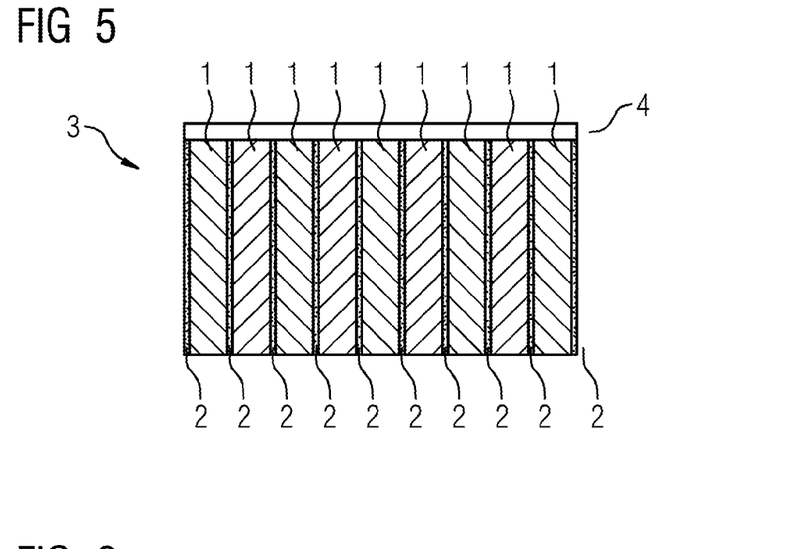
FIG. 5 a schematic view of a scintillator unit according to an embodiment of the invention.

FIG. 5 shows a side view of an example embodiment of the scintillator unit 3 according to the invention. The scintillator unit 3 comprises a reflector layer 4 on the inlet side for X-radiation or X-rays emitted by the radiation source. The scintillator fibers 1 are aligned parallel to one another along their length.

Figure 6:
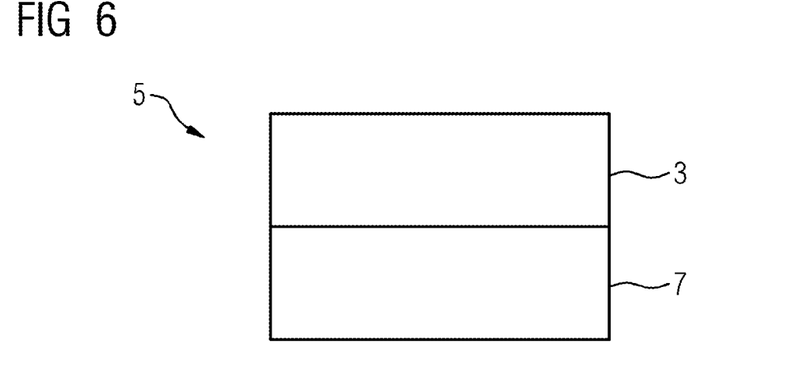
FIG. 6 a schematic view of an X-ray detector according to an embodiment of the invention.

FIG. 6 shows an example embodiment of the X-ray detector according to the invention 5. The X-ray detector 5 comprises a scintillator unit 3 and a evaluation unit 7 connected to one another in a planar manner. Each sub-region or pixel of the scintillator unit includes a plurality of scintillator fibers. A plurality of scintillator fibers can be assigned to one sub-region of the evaluation unit 7.

Figure 7:
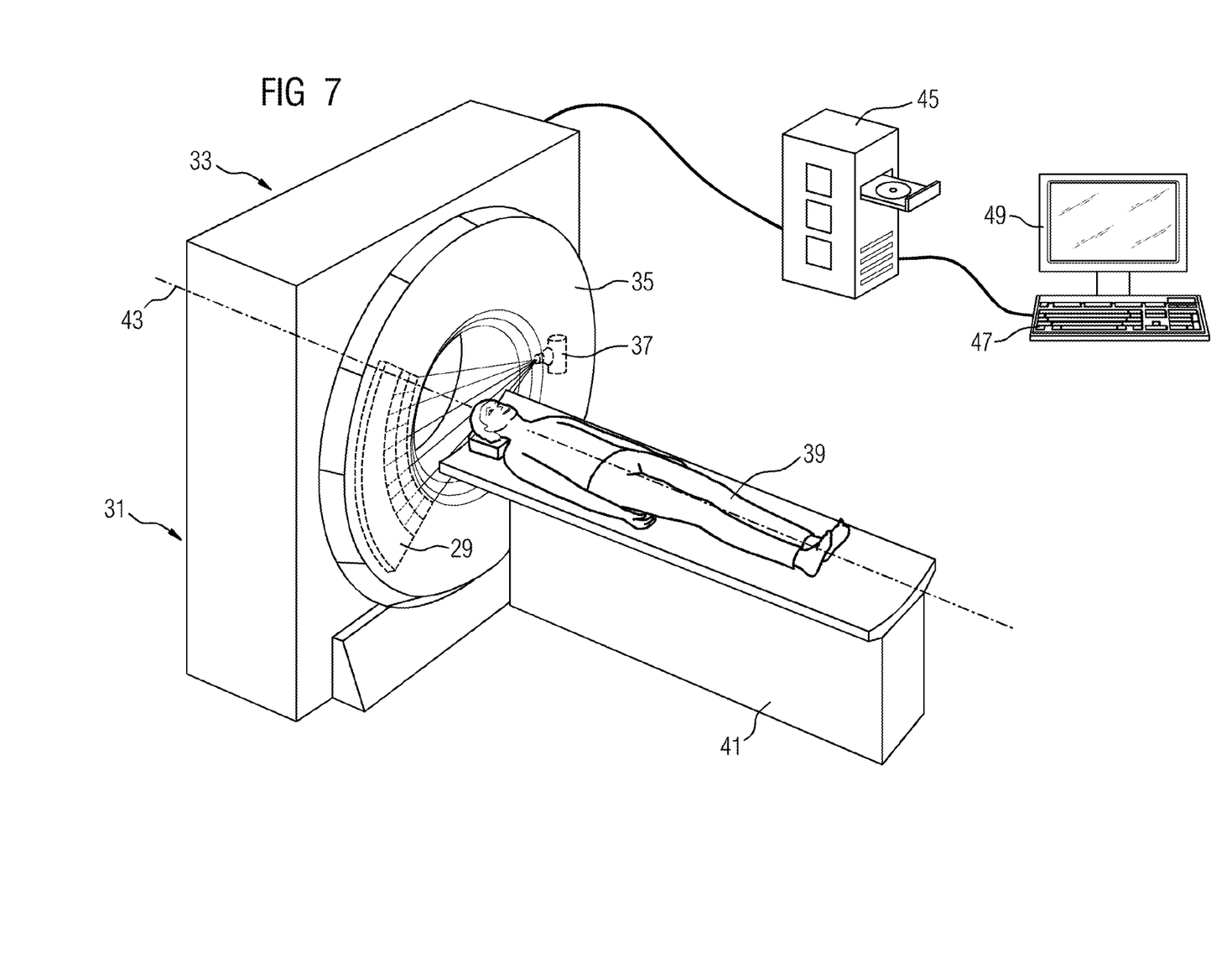
FIG. 7 a schematic view of a depiction of a computed tomography scanner according to an embodiment of the invention.

FIG. 7 shows an example embodiment of the computed tomography scanner according to the invention 31. The detector apparatus 29 preferably comprises a plurality of X-ray detectors 5 in a two-dimensional matrix or arrangement. The computed tomography 31 scanner contains a gantry 33 with a rotor 35. The rotor 35 comprises a radiation source 37 and the detector apparatus 29 according to an example embodiment of the invention. The patient 39 is supported on the patient bed 41 and can be moved through the gantry 33 along the second axis 43, the axis of rotation. A computing unit 45 is used to control and calculate the sectional views. An input mechanism 47 and an output apparatus 49 are connected to the computing unit 45.

Although the invention was illustrated in more detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. §112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for production of a scintillator fiber, comprising:
   provisioning a suspension of a binder dissolved in a solvent and a scintillator material; and
   pressing the suspension into a precipitation bath in which the binder is insoluble.

2. The method of claim 1, further comprising:
   solidifying the scintillator fiber.

3. The method of claim 2,
   wherein the solvent comprises at least one element from the group consisting of aprotic polar solvent and N-methylpyrrolidone;
   wherein the binder comprises at least one element from the group consisting of amorphous high-performance thermoplastic and polysulfone;
   wherein the scintillator material comprises at least one element from the group consisting of ceramic scintillator material, GGAG and GOS; and
   wherein the precipitation bath comprises at least one element from the group consisting of protic solvent, water, ethanol and isopropanol.

4. The method of claim 2,
   wherein the solvent comprises at least one element from the group consisting of protic solvent, ethanol and isopropanol;
   wherein the binder comprises at least one element from the group consisting of polyvinyl acetals and polyvinyl butyral;
   wherein the scintillator material comprises at least one element from the group consisting of ceramic scintillator material, GGAG and GOS; and
   wherein the precipitation bath comprises at least one element from the group consisting of protic solvent and water.

5. The method of claim 2, further comprising at least one of:
   debinding the scintillator fiber;
   first pressing the scintillator fiber; and
   sintering the scintillator fiber.

6. The method of claim 5, comprising
   sintering; and
   second pressing, upon the first pressing occurring, the scintillator fibers.

7. The method of claim 1, further comprising at least one of:
   debinding the scintillator fiber;
   first pressing the scintillator fiber; and
   sintering the scintillator fiber.

8. The method of claim 7, comprising
   sintering; and
   second pressing, upon the first pressing occurring, the scintillator fibers.

9. The method of claim 7,
   wherein the solvent comprises at least one element from the group consisting of aprotic polar solvent and N-methylpyrrolidone;
   wherein the binder comprises at least one element from the group consisting of amorphous high-performance thermoplastic and polysulfone;
   wherein the scintillator material comprises at least one element from the group consisting of ceramic scintillator material, GGAG and GOS; and
   wherein the precipitation bath comprises at least one element from the group consisting of protic solvent, water, ethanol and isopropanol.

10. The method of claim 7,
    wherein the solvent comprises at least one element from the group consisting of protic solvent, ethanol and isopropanol;
    wherein the binder comprises at least one element from the group consisting of polyvinyl acetals and polyvinyl butyral;
    wherein the scintillator material comprises at least one element from the group consisting of ceramic scintillator material, GGAG and GOS; and
    wherein the precipitation bath comprises at least one element from the group consisting of protic solvent and water.

11. The method of claim 1,
    wherein the solvent comprises at least one element from the group consisting of aprotic polar solvent and N-methylpyrrolidone;
    wherein the binder comprises at least one element from the group consisting of amorphous high-performance thermoplastic and polysulfone;
    wherein the scintillator material comprises at least one element from the group consisting of ceramic scintillator material, GGAG and GOS; and
    wherein the precipitation bath comprises at least one element from the group consisting of protic solvent, water, ethanol and isopropanol.

12. The method of claim 1,
    wherein the solvent comprises at least one element from the group consisting of protic solvent, ethanol and isopropanol;
    wherein the binder comprises at least one element from the group consisting of polyvinyl acetals and polyvinyl butyral;
    wherein the scintillator material comprises at least one element from the group consisting of ceramic scintillator material, GGAG and GOS; and
    wherein the precipitation bath comprises at least one element from the group consisting of protic solvent and water.

13. The method of claim 1, wherein a diameter of the scintillator fiber is 40 to 100 μm.

14. A method for production of a scintillator unit, comprising:
bundling a plurality of scintillator fibers, each produced by the method of claim 1, and
filling interstices between respective ones of the plurality of scintillator fibers with an adhesive.

15. The method of claim 14, wherein the adhesive comprises an epoxy compound.

16. The method of claim 14, further comprising at least one of:
sawing, in order to set a layer thickness the scintillator unit; and
applying a reflector layer.

17. A scintillator unit produced by the method of claim 14.

18. An X-ray detector, comprising:
the scintillator unit of claim 17; and
an evaluation unit.

19. A medical device, comprising:
the X-ray detector of claim 18.

20. The method of claim 15, further comprising at least one of:
sawing, in order to set a layer thickness the scintillator unit; and
applying a reflector layer.

* * * * *